US009791393B2

(12) United States Patent
Sako

(10) Patent No.: US 9,791,393 B2
(45) Date of Patent: Oct. 17, 2017

(54) X-RAY DETECTION SIGNAL PROCESSING DEVICE AND X-RAY ANALYZING APPARATUS USING SAME

(71) Applicant: RIGAKU CORPORATION, Tokyo (JP)

(72) Inventor: Yukio Sako, Takatsuki (JP)

(73) Assignee: Rigaku Corporation, Tokyo (JP)

( * ) Notice: Subject to any disclaimer, the term of this patent is extended or adjusted under 35 U.S.C. 154(b) by 0 days.

(21) Appl. No.: 15/325,787

(22) PCT Filed: May 14, 2015

(86) PCT No.: PCT/JP2015/063893
§ 371 (c)(1),
(2) Date: Jan. 12, 2017

(87) PCT Pub. No.: WO2016/013278
PCT Pub. Date: Jan. 28, 2016

(65) Prior Publication Data
US 2017/0153190 A1 Jun. 1, 2017

(30) Foreign Application Priority Data
Jul. 23, 2014 (JP) .................................. 2014-149421

(51) Int. Cl.
*H03F 1/26* (2006.01)
*G01N 23/223* (2006.01)
(Continued)

(52) U.S. Cl.
CPC ........... *G01N 23/223* (2013.01); *G01R 13/00* (2013.01); *H01J 35/14* (2013.01); *H01J 35/30* (2013.01);
(Continued)

(58) Field of Classification Search
CPC .......... G01R 13/00; H01J 35/14; H01J 35/30; H05G 1/26
(Continued)

(56) References Cited

U.S. PATENT DOCUMENTS 4,288,692 A * 9/1981 Schamber ............ G01N 23/225
250/310
6,486,808 B1 * 11/2002 Seppi .................... H03M 1/129
330/302
(Continued)

FOREIGN PATENT DOCUMENTS

CN 1595291 A 3/2005
JP 06-123778 A 5/1994
(Continued)

OTHER PUBLICATIONS

International Preliminary Report on Patentability and English Translation of Written Opinion dated Feb. 2, 2017 in counterpart International Application No. PCT/JP2015/063893.
(Continued)

*Primary Examiner* — Michael Nghiem
(74) *Attorney, Agent, or Firm* — Sughrue Mion, PLLC

(57) ABSTRACT

An X-ray detection signal processing device (10) and the like according to the present invention includes: a comparator (17) configured to output a High signal when a level of a signal from a continuous reset type preamplifier (13) having an CR circuit (13a) does not exceed a predetermined upper limit value, and output a Low signal when the level of the signal from the preamplifier (13) exceeds the predetermined upper limit value; and a control section (18) configured to delay shift of the signal of the comparator (17) from Low to High by a predetermined time, to perform output to a clock oscillator (15), stop oscillation by outputting a Low signal to the clock oscillator (15), and thus stop high-speed
(Continued)

AD conversion by a high-speed AD converter (14) and maintain an output value.

2 Claims, 6 Drawing Sheets

(51) Int. Cl.
   *H01J 35/30* (2006.01)
   *G01R 13/00* (2006.01)
   *H05G 1/26* (2006.01)
   *H01J 35/14* (2006.01)
(52) U.S. Cl.
   CPC ......... *H05G 1/26* (2013.01); *G01N 2223/076* (2013.01); *G01N 2223/304* (2013.01)
(58) Field of Classification Search
   USPC ........................................................ 702/189
   See application file for complete search history.

(56) References Cited

U.S. PATENT DOCUMENTS

| | | |
|---|---|---|
| 7,110,498 B2 | 9/2006 | Yamada |
| 8,039,787 B2 | 10/2011 | Mott |
| 2005/0058252 A1 | 3/2005 | Yamada |
| 2009/0033913 A1 | 2/2009 | Mott |
| 2011/0141453 A1* | 6/2011 | Clement ............... G01S 17/105 356/5.01 |

FOREIGN PATENT DOCUMENTS

| | | |
|---|---|---|
| JP | 07-239385 A | 9/1995 |
| JP | 2011-511927 A | 4/2011 |
| JP | 2013-113648 A | 6/2013 |
| JP | 2013-246096 A | 12/2013 |
| WO | 2009/020859 A1 | 2/2009 |

OTHER PUBLICATIONS

Notification of Reason(s) for Rejection of JP Appln. No. 2014-149421 dated Oct. 13, 2015.
Decision of Grant of JP Appln. No. 2014-149421 dated Dec. 1, 2015.
International Search Report of PCT/JP2015/063893 dated Jun. 16, 2015 [PCT/ISA/210].
Communication dated May 19, 2017 issued by the State Intellectual Property Office of People's Republic of China in counterpart application No. 201580039683.4.
Lü Fu-yong et al.; "Half-bridge Series Resonant Switching Power with a Low Ripple and High Stability", Power Electronica, Aug. 25, 2005, vol. 39, No. 4, pp. 103-105( 3 pages total).

* cited by examiner

X-RAY DETECTION SIGNAL PROCESSING DEVICE AND X-RAY ANALYZING APPARATUS USING SAME

CROSS REFERENCE TO THE RELATED APPLICATION

This application is based on and claims Convention priority to Japanese patent application No. 2014-149421, filed Jul. 23, 2014, the entire disclosure of which is herein incorporated by reference as a part of this application.

BACKGROUND OF THE INVENTION

Field of the Invention

The present invention relates to an X-ray detection signal processing device to which a signal from an X-ray detector is inputted, and which outputs a signal having a pulse height corresponding to energy of X-rays that are incident on the X-ray detector, and an X-ray analyzing apparatus using the X-ray detection signal processing device.

Description of Related Art

To date, for example, in X-ray fluorescence analysis, there is an X-ray detection signal processing device which amplifies, by a preamplifier, a signal from an X-ray detector (an output signal from an X-ray detector. Hereinafter, an output signal from each component will be similarly called), subjects the amplified signal to high-speed AD conversion by a high-speed AD converter, and smoothes the obtained signal by using a filter function of a signal processing section, thereby outputting a signal (a pulse height value), having a pulse height corresponding to energy (wavelength) of X-rays that are incident on the X-ray detector. The X-ray detection signal processing devices are classified into the following two conventional arts according to a type of the preamplifier (see paragraphs 0005, 0006 of Patent Document 1). In any of the conventional arts, two conditions that are a condition that a level of a signal from the preamplifier is within an unsaturated range, that is, within a range effective for the analysis, and a condition that the level of the signal is within a range for input to the high-speed AD converter, need to be satisfied in order to perform correct signal processing.

In an X-ray detection signal processing device 20 of the first conventional art, as shown in FIG. 4, a pulse reset type preamplifier 23 having a circuit 23a that includes a capacitor and a reset switch is used. In the preamplifier 23, as indicated by an output waveform in the upper right portion in FIG. 4, signals from the X-ray detector are amplified and then charged and piled up one by one in the capacitor. When the piled up level exceeds a predetermined upper limit value, a reset signal is outputted from a comparator 27 to the reset switch of the preamplifier 23, and the capacitor is discharged, and the preamplifier 23 is reset. The predetermined upper limit value in the comparator 27 is set so as to satisfy the above two conditions.

In an X-ray detection signal processing device 30 of the second conventional art, as shown in FIG. 5, a continuous reset type (also referred to as a tail pulse type, RC-coupled type, or the like) preamplifier 13 having a CR circuit 13a that includes a capacitor and a resistor, is used. In the preamplifier 13, as indicated by an output waveform in the upper left portion in FIG. 5, each signal from the X-ray detector is amplified and steeply rises, to charge the capacitor, similarly to the pulse reset type preamplifier 23 (FIG. 4). However, for each signal, the capacitor is discharged according to a time constant of the CR circuit 13a, to attenuate the charged level, unlike the pulse reset type preamplifier 23. For this characteristic, an approach, such as using of a comparator in which a threshold value is set, for satisfying the above two conditions, is not made except that a time constant is appropriately set in the CR circuit 13a. However, in general, the high-speed AD converter 14 has its own determination function and determines whether or not the level of a signal from the preamplifier 13 is within a range for input to the high-speed AD converter 14, and when the range for the input is exceeded, a signal outside the range is obtained and can be addressed without stopping the high-speed AD conversion.

RELATED DOCUMENT

Patent Document

[Patent Document 1] Japanese Translation of PCT International Application Publication No. 2011-511927

However, in the first conventional art, each signal from the X-ray detector is amplified and then charged and piled up in the capacitor without attenuation. Therefore, in a case where a predetermined upper limit value is set in the comparator 27 in order to satisfy the above two conditions, a level which each signal from the X-ray detector is allowed to have when the signal is outputted from the preamplifier 23, is for example, about 1/100 of a value in the effective range in which the output from the preamplifier 23 is not saturated, or about 1/100 of a value in the range for input to the high-speed AD converter 14, that is, about 10 mV. As a result, there is a problem that an SN ratio is not advantageous, and a high counting rate cannot be addressed.

Meanwhile, in the second conventional art, each signal from the X-ray detector is amplified and charged in the capacitor, and thereafter the level is attenuated according to a time constant of the CR circuit 13a. Therefore, as compared to the first conventional art, the value of the capacitor is reduced, whereby an output level from the preamplifier 23 for each signal can be increased to, for example, about 100 mV, and an SN ratio can be made advantageous and a high counting rate can be addressed. Further, as described above, when the level of a signal from the preamplifier 13 exceeds a range for input to the high-speed AD converter 14, the high-speed AD converter 14 itself can address this.

However, the following problem arises. In FIG. 6, a signal Po from the preamplifier 13 and a signal ADo from the high-speed AD converter 14, in the second conventional art, are indicated so as to be vertically arranged. In each of the vertically arranged portions in FIG. 6, the ordinate represents levels of the signals, and the abscissa represents time. A state where the level of the signal Po from the preamplifier 13 is in an effective range in which no saturation occurs, is shown on the left side, and a state where the level of the signal Po from the preamplifier 13 exceeds the effective range in which no saturation occurs, such as a state where the frequency with which the X-rays are incident on the X-ray detector is increased to cause superimposing, or a state where cosmic rays having high energy are incident on the X-ray detector, is shown on the right side.

In the second conventional art, the high-speed AD converter 14 constantly subjects the signal Po from the preamplifier 13 to high-speed AD conversion as it is, and the signal processing section 16 determines that the signal has arrived on the basis of steep rising of the signal ADo from the high-speed AD converter 14, smoothes the signal that is determined to have arrived, by using a filter function, to obtain a pulse height, and outputs the obtained pulse height to a multichannel pulse height analyzer. For example, as shown on the left side in FIG. 6, in a state where the level of the signal Po from the preamplifier 13 is in an effective range in which no saturation occurs, steep rising N of the signal Po from the preamplifier 13 is subjected to high-speed AD conversion as it is, to obtain steep rising Nd of the signal ADo from the high-speed AD converter 14. Based on the steep rising Nd, the signal processing section 16 determines that the signal ADo from the high-speed AD converter 14 has arrived, and smooths the signal ADo that is determined to have arrived, by using the filter function, to obtain a pulse height, and outputs the obtained pulse height to the multichannel pulse height analyzer. The multichannel pulse height analyzer processes the pulse height as a normal effective one. There is no problem in this operation.

Meanwhile, as shown on the right side in FIG. 6, in a state where the level of the signal Po from the preamplifier 13 exceeds the effective range in which no saturation occurs, steep rising A of the signal Po from the preamplifier 13, and steep falling B and steep rising C that are generated, during the following attenuation, as noise (called glitch, sag, or the like) caused by characteristic of the preamplifier 13 are subjected to high-speed AD conversion as they are, to obtain steep rising Ad, steep falling Bd, and steep rising Cd of the signal ADo from the high-speed AD converter 14. The signal processing section 16 determines that the signal ADo from the high-speed AD converter 14 has arrived twice on the basis of the two steep risings Ad and Cd, and smooths the two signals (former part and latter part of ADo) that are determined to have arrived, by using the filter function, to obtain pulse heights, and outputs the obtained pulse heights to the multichannel pulse height analyzer. In the multichannel pulse height analyzer, among the two pulse heights, the pulse height for the former steep rising Ad can be processed as an abnormal ineffective one on the basis of the magnitude of the value, while the pulse height for the latter steep rising Cd cannot be processed as an abnormal ineffective one, and may be processed as a normal effective one, similarly to the pulse height for the above-described steep rising Nd. As a result, in the multichannel pulse height analyzer, energy resolution may become lower.

SUMMARY OF THE INVENTION

The present invention is made in view of the aforementioned problems of the conventional arts, and an object of the present invention is to provide: an X-ray detection signal processing device that has an advantageous SN ratio, can address a high counting rate, and can further perform analysis at a high energy resolution even when the frequency with which X-rays are incident on an X-ray detector is increased, or when cosmic rays are incident on the X-ray detector; and an X-ray analyzing apparatus using the X-ray detection signal processing device.

In order to attain the aforementioned object, an X-ray detection signal processing device according to a first aspect of the present invention is an X-ray detection signal processing device to which a signal from an X-ray detector is inputted, and which outputs a signal having a pulse height corresponding to energy of X-rays which are incident on the X-ray detector, and the X-ray detection signal processing device includes: a preamplifier configured to amplify the signal from the X-ray detector, and attenuate the signal according to a time constant of a CR circuit; a clock oscillator; a high-speed AD converter configured to operate based on oscillation of the clock oscillator and subject a signal from the preamplifier to high-speed AD conversion; and a signal processing section configured to determine, based on rising of a signal from the high-speed AD converter, that the signal has arrived, and smooth the signal which is determined to have arrived, by using a filter function. Further, the X-ray detection signal processing device includes: a comparator configured to output a High signal when a level of the signal from the preamplifier does not exceed a predetermined upper limit value, and output a Low signal when the level of the signal from the preamplifier exceeds the predetermined upper limit value; and a control section configured to delay shift of the signal of the comparator from Low to High by a predetermined time, to perform output to the clock oscillator, stop oscillation by outputting a Low signal to the clock oscillator, and thus stop the high-speed AD conversion by the high-speed AD converter and maintain an output value.

In the X-ray detection signal processing device according to the first aspect, the continuous reset type preamplifier having the CR circuit is used, and when the level of the signal from the preamplifier exceeds the predetermined upper limit value, the control section stops the high-speed AD conversion by the high-speed AD converter and maintains the output. Thereafter, when the level of the signal from the preamplifier is attenuated so as to be less than or equal to the predetermined upper limit value, restart of the high-speed AD conversion is delayed by a predetermined time, whereby an SN ratio is advantageous, and a high counting rate can be addressed. Further, even when the frequency with which X-rays are incident on the X-ray detector is increased, or cosmic rays are incident on the X-ray detector, only a pulse height that can be correctly processed by the pulse height analyzer concerning whether the pulse height is effective or ineffective, is outputted, thereby enabling analysis at a high energy resolution.

An X-ray analyzing apparatus according to a second aspect of the present invention includes the X-ray detection signal processing device according to the first aspect. Also in the X-ray analyzing apparatus according to the second aspect, the same operation and effect as those of the X-ray detection signal processing device according to the first aspect, can be obtained.

Any combination of at least two constructions, disclosed in the appended claims and/or the specification and/or the accompanying drawings should be construed as included within the scope of the present invention. In particular, any combination of two or more of the appended claims should be equally construed as included within the scope of the present invention.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF EMBODIMENTS

Figure 1:
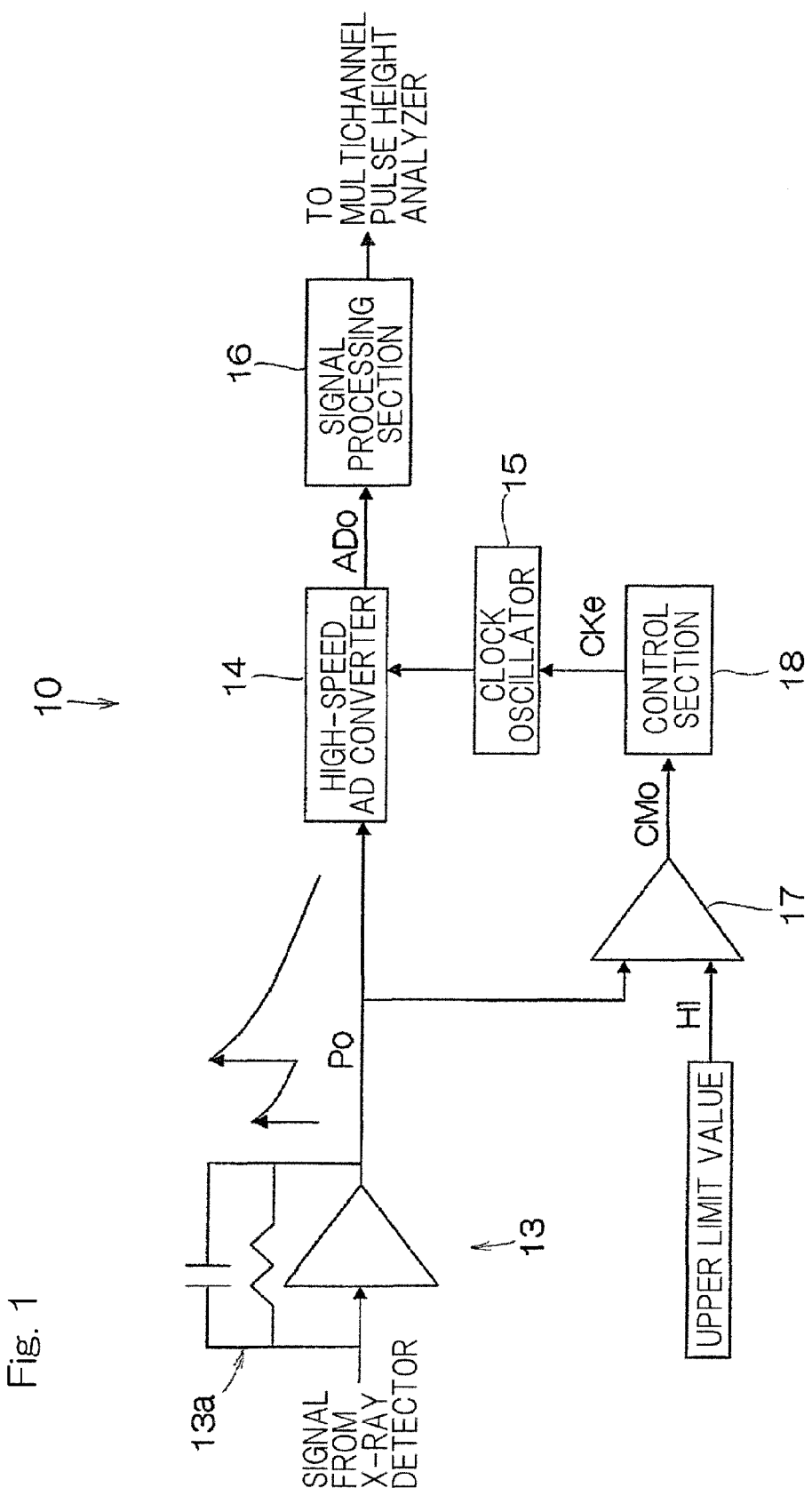
FIG. 1 schematically illustrates an X-ray detection signal processing device according to one embodiment of the present invention.

Hereinafter, an X-ray detection signal processing device according to one embodiment of the present invention will be described with reference to the drawings. As shown in FIG. 1, this device is a device 10 to which a signal from an X-ray detector is inputted, and which outputs a signal having a pulse height corresponding to energy of X-rays that are incident on the X-ray detector, and the device 10 includes: an preamplifier 13 that amplifies a signal from the X-ray detector, and attenuates the signal according to a time constant of a CR circuit 13a; a clock oscillator 15; a high-speed AD converter 14 that operates on the basis of oscillation of the clock oscillator 15, and subjects the signal from the preamplifier 13 to high-speed AD conversion; and a signal processing section 16 that determines, on the basis of rising of the signal from the high-speed AD converter 14, that the signal has arrived, and bases on the height of the rising of the signal that is determined to have arrived, in other words, smooths the signal that is determined to have arrived by using a filter function, to obtain a pulse height, and outputs the pulse height to a multichannel pulse height analyzer. In the present embodiment, the X-ray detection signal processing device according to the present invention is applied to a multichannel pulse height analyzer. However, the present invention is not limited thereto, and the X-ray detection signal processing device according to the present invention can be applied to a single channel pulse height analyzer as well as a multichannel pulse height analyzer (multichannel analyzer).

Thus, in the X-ray detection signal processing device 10 according to the present embodiment, similarly to the second conventional art as described above, the continuous reset type preamplifier 13 having the CR circuit 13a is used, and therefore the output level from the preamplifier 13 for each signal from the X-ray detector can be increased to, for example, about 100 mV, and an SN ratio is advantageous, and a high counting rate can be addressed. Further, as described above, if the level of the signal from the preamplifier 13 exceeds a range for input to the high-speed AD converter 14, the high-speed AD converter 14 itself can address this.

The X-ray detection signal processing device 10 according to the present embodiment further includes: a comparator 17 that outputs a High signal when the level of the signal from the preamplifier 13 does not exceed a predetermined upper limit value, and outputs a Low signal when the level of the signal from the preamplifier 13 exceeds the predetermined upper limit value; and a control section 18 that delays shift of the signal of the comparator 17 from Low to High by a predetermined time to perform output to the clock oscillator 15, stops the oscillation by outputting the Low signal to the clock oscillator 15, and thus stops the high-speed AD conversion by the high-speed AD converter 14 and maintains an output value of the high-speed AD converter 14.

Figure 3:
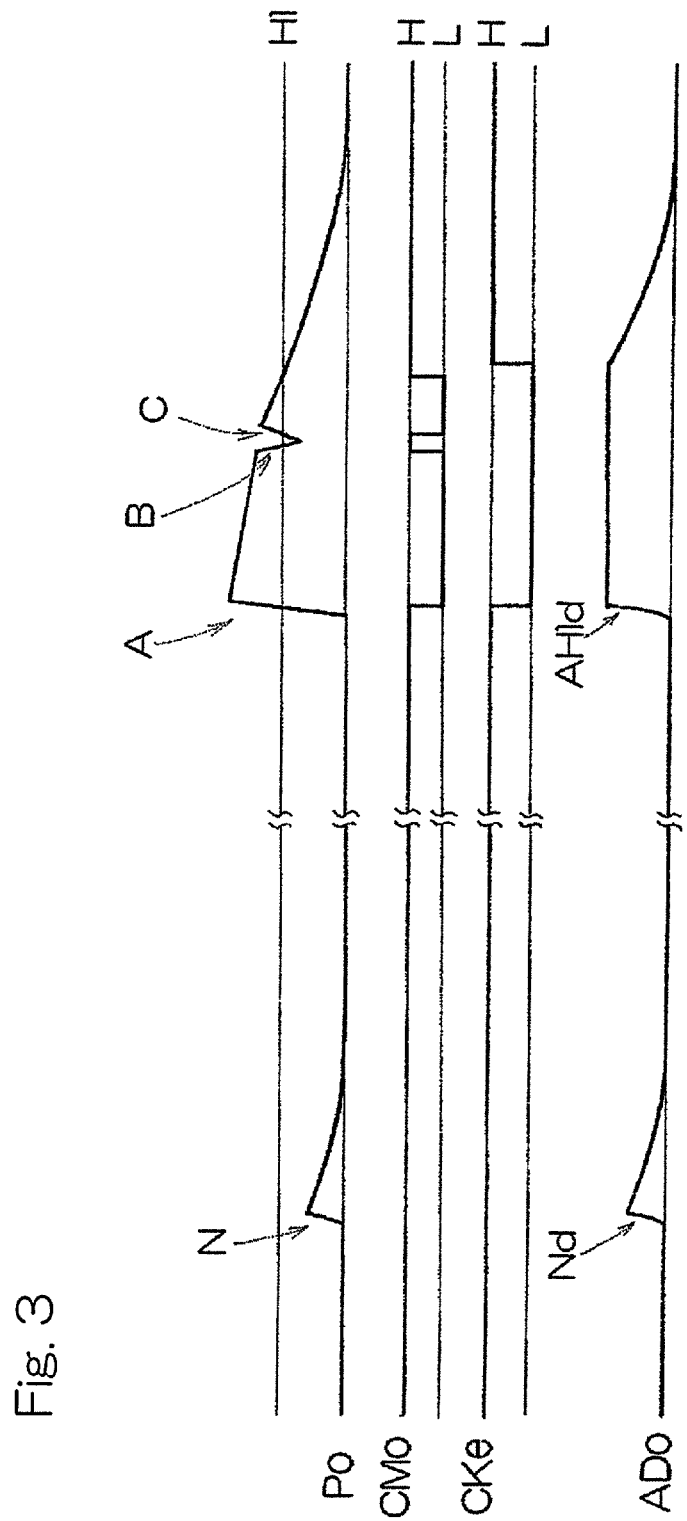
FIG. 3 illustrates signals, from components of the X-ray detection signal processing device, which are indicated so as to be vertically arranged.
Figure 4:
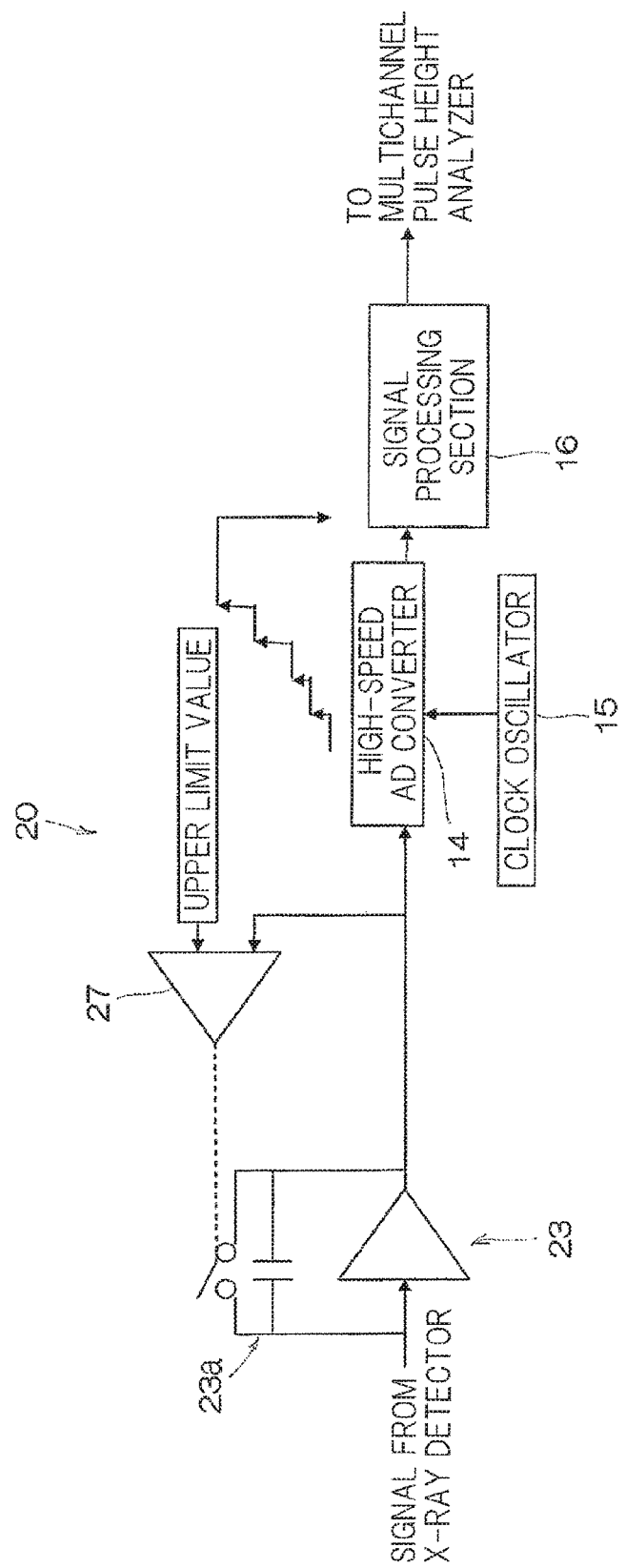
FIG. 4 schematically illustrates an X-ray detection signal processing device of a first conventional art.
Figure 5:
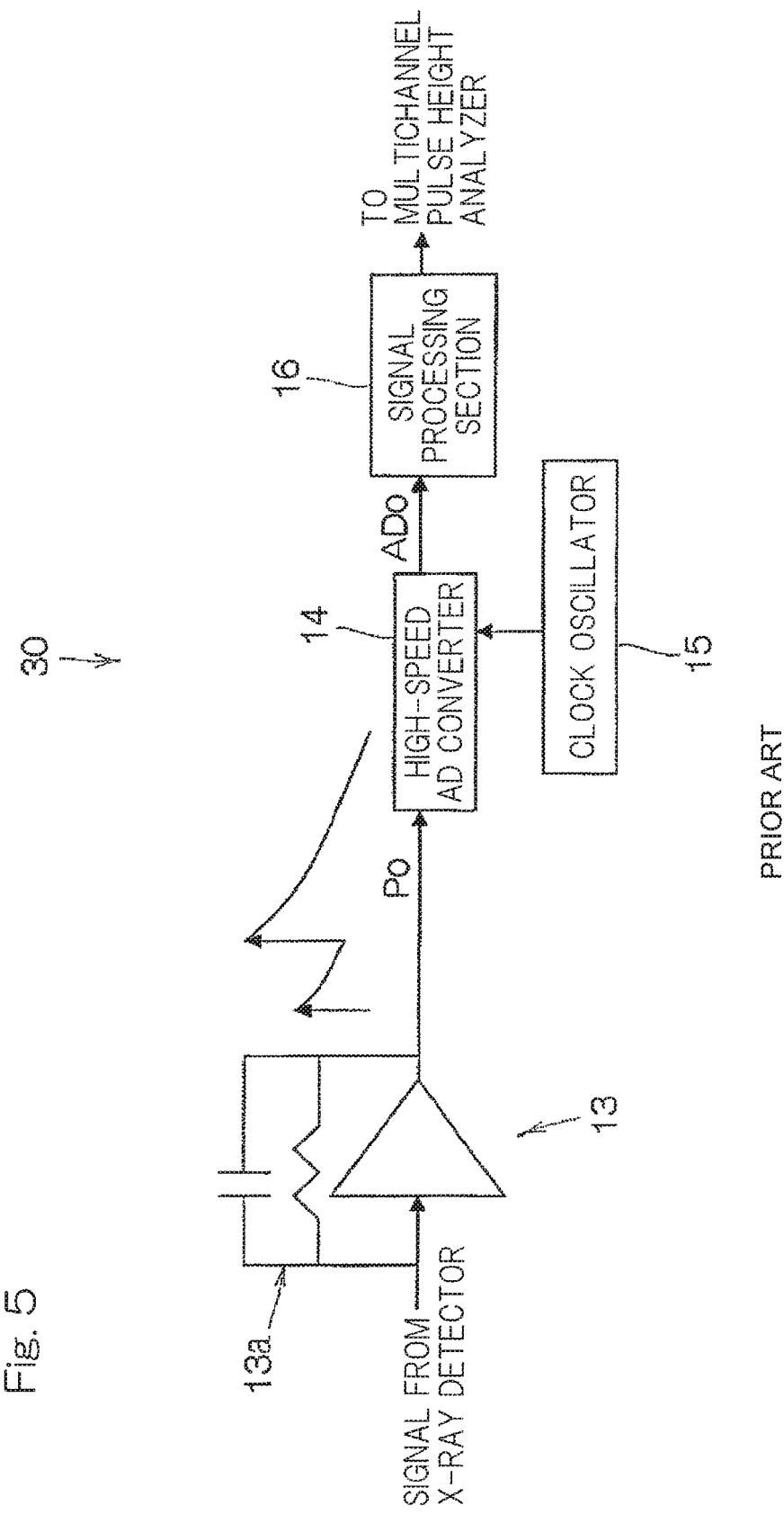
FIG. 5 schematically illustrates an X-ray detection signal processing device of a second conventional art.
Figure 6:
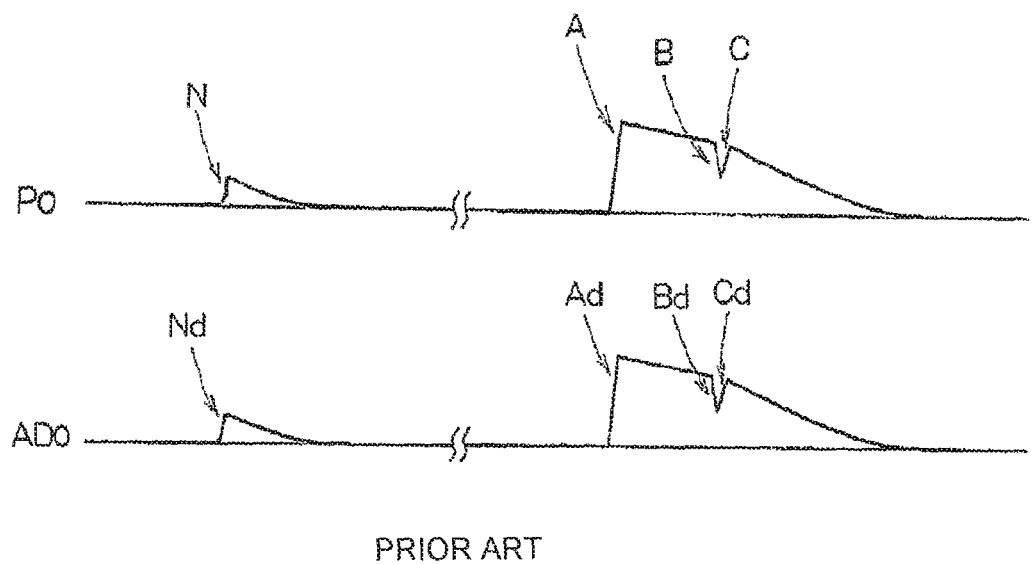
FIG. 6 illustrates signals, from components of the X-ray detection signal processing device of the second conventional art, which are indicated so as to be vertically arranged.

An operation performed by the X-ray detection signal processing device 10, according to the present embodiment, which includes the comparator 17 and the control section 18, will be described. FIG. 3 illustrates a signal Po from the preamplifier 13, a signal CMo from the comparator 17, a signal CKe from the control section 18, and a signal ADo from the high-speed AD converter 14, in the X-ray detection signal processing device 10 according to the present embodiment, which are indicated so as to be vertically arranged. In each of the vertically arranged portions in FIG. 3, the ordinate represents levels of the signals, and the abscissa represents time. A state where the level of the signal Po from the preamplifier 13 is in an effective range in which no saturation occurs is shown on the left side, and a state where the level of the signal Po from the preamplifier 13 exceeds the effective range in which no saturation occurs, such as a state where the frequency with which X-rays are incident on the X-ray detector is increased to cause superimposing, or a state where cosmic rays having high energy are incident on the X-ray detector, is shown on the right side. Hl represents the predetermined upper limit value, for the signal Po from the preamplifier 13, which is set in the comparator 17, and H represents High and L represents Low for the signal CMo from the comparator 17 and the signal CKe from the control section 18.

As shown on the left side in FIG. 3, in a state where the level of the signal Po from the preamplifier 13 is in the effective range in which no saturation occurs, that is, in a state where the level of the signal Po is lower than or equal to the predetermined upper limit value Hl set in the comparator 17, the signal CMo from the comparator 17 and the signal CKe from the control section 18 both represent High, and steep rising N of the signal Po from the preamplifier 13 is subjected to high-speed AD conversion as it is, to obtain steep rising Nd of the signal ADo from the high-speed AD converter 14. The signal processing section 16 determines, on the basis of the steep rising Nd, that the signal ADo from the high-speed AD converter 14 has arrived, and smooths the signal ADo that is determined to have arrived, by using the filter function, to obtain a pulse height, and outputs the pulse height to the multichannel pulse height analyzer. The multichannel pulse height analyzer processes the pulse height as a normal effective one. This operation is the same as the operation, in which there is no problem, performed by the second conventional art as described above.

Meanwhile, as shown on the right side in FIG. 3, when the level of the signal Po from the preamplifier 13 exceeds the effective range in which no saturation occurs, that is, when the level of the signal Po exceeds the predetermined upper limit value Hl set in the comparator 17, the signal CMo from the comparator 17 and the signal CKe from the control section 18 both become Low. When the Low signal CKe from the control section 18 is outputted to the clock oscillator 15, the clock oscillator 15 stops oscillation by which the high-speed AD converter 14 is operated, whereby the high-speed AD converter 14 stops the high-speed AD conversion and an output value obtained immediately before the stopping is maintained, that is, an output value obtained when the level of the signal Po from the preamplifier 13 has reached the predetermined upper limit value Hl set in the comparator 17, is maintained. As a result, the steep rising A of the signal Po from the preamplifier 13 is subjected to the high-speed AD conversion until reaching to the upper limit value Hl, to obtain, as AHld, the steep rising of the signal ADo from the high-speed AD converter 14.

When, during the attenuation following the steep rising A, the level of the signal Po from the preamplifier 13 is returning so as to be in the effective range in which no saturation occurs, that is, the level of the signal Po is becoming less than or equal to the predetermined upper limit value Hl set in the comparator 17, steep falling B and steep rising C are generated as noise (called glitch, sag, or the like) caused by characteristic of the preamplifier 13. At the steep falling B and the steep rising C, the level of the signal Po from the preamplifier 13 is reduced so as to be less than the predetermined upper limit value Hl set in the comparator 17, and is then increased again so as to exceed the predetermined upper limit value Hl. Therefore, the signal CMo from the comparator 17 changes from Low to High, and returns again to Low soon. However, the control section 18 delays shift of the signal CMo of the comparator 17 from Low to High by a predetermined time, to perform output to the clock oscillator 15, so that the signal CKe from the control section 18 remains Low. Therefore, the high-speed AD converter 14 continues to maintain the output value of the terminating end of the steep rising AHld. The predetermined time by which shift of the signal CMo of the comparator 17 from Low to High is delayed, and which is set in the control section 18, can be experimentally determined, and the predetermined time is, for example, 0.03 msec.

When, during attenuation following the steep rising C, the level of the signal Po from the preamplifier 13 returns so as to be in the effective range in which no saturation occurs, that is, the level of the signal Po is reduced to the predetermined upper limit value Hl set in the comparator 17, the signal CMo from the comparator 17 is shifted from Low to High, and the signal CKe from the control section 18 is delayed by the above-described predetermined time and is also shifted from Low to High. When the signal CKe from the control section 18 becomes High, the high-speed AD converter 14 restarts the high-speed AD conversion for the signal Po from the preamplifier 13, and the signal ADo from the high-speed AD converter 14 is attenuated similarly to the signal Po from the preamplifier 13.

Therefore, in the signal ADo from the high-speed AD converter 14, only the first steep rising AHld appears, and the signal processing section 16 determines, on the basis thereof, that the signal ADo from the high-speed AD converter 14 has arrived, and smooths the signal ADo that is determined to have arrived, by using the filter function, to obtain a pulse height, and outputs the pulse height to the multichannel pulse height analyzer. The multichannel pulse height analyzer can process the pulse height as an abnormal ineffective one according to the magnitude of the value, and does not process the pulse height as a normal effective one in the same manner as for the pulse height for the steep rising Nd as described above, so that energy resolution is less likely to become lower.

As described above, in the X-ray detection signal processing device 10 according to the present embodiment, the continuous reset type preamplifier 13 having the CR circuit 13a is used, and when the level of the signal Po from the preamplifier 13 exceeds the predetermined upper limit value Hl, the control section 18 stops the high-speed AD conversion by the high-speed AD converter 14 and maintains the output. Thereafter, when the level of the signal Po from the preamplifier 13 is attenuated so as to be less than or equal to the predetermined upper limit value Hl, restart of the high-speed AD conversion is delayed by a predetermined time, whereby an SN ratio is advantageous, and a high counting rate can be addressed. Further, even when the frequency with which X-rays are incident on the X-ray detector is increased, or cosmic rays are incident on the X-ray detector, only a pulse height that can be correctly processed by the pulse height analyzer concerning whether the pulse height is effective or ineffective, is outputted, thereby enabling analysis at a high energy resolution.

Figure 2:
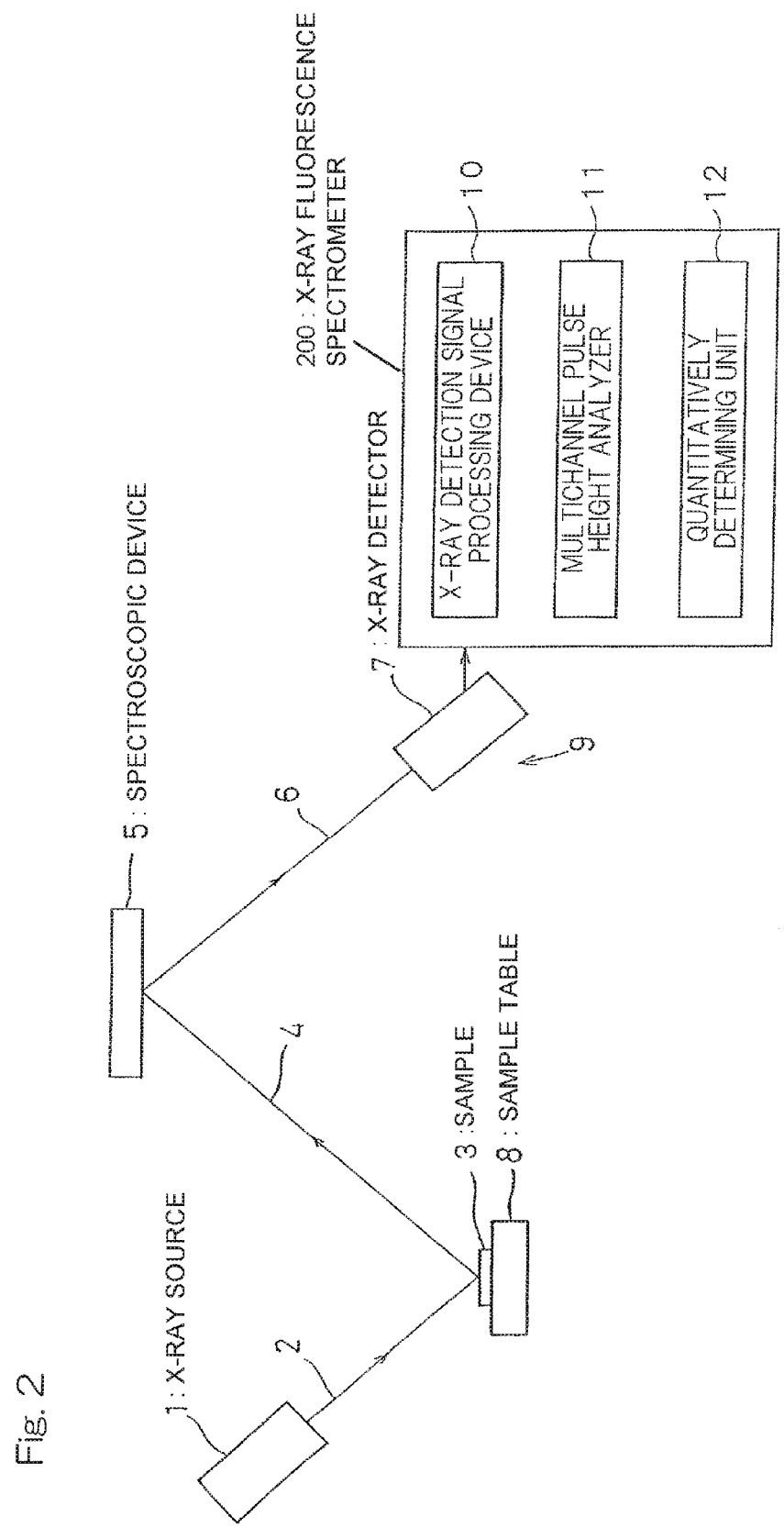
FIG. 2 schematically illustrates an X-ray fluorescence spectrometer using the X-ray detection signal processing device.

The X-ray detection signal processing device 10 according to the present embodiment is used for, for example, an X-ray fluorescence spectrometer shown in FIG. 2. The X-ray fluorescence spectrometer is an X-ray fluorescence spectrometer that detects, by using a detection unit 9, fluorescent X-rays 4 generated by irradiating a sample 3 placed on a sample table 8, with primary X-rays 2 from an X-ray source 1 such as an X-ray tube. The X-ray fluorescence spectrometer includes: the above-described X-ray detection signal processing device 10; a multichannel pulse height analyzer 11 that sorts a signal (pulse height value), having a pulse height, from the X-ray detection signal processing device 10 by each of multiple continuous pulse height ranges to obtain a counting rate, and obtain energy spectrum (pulse height distribution curve) that represents a distribution of counting rates with respect to the pulse height; and a quantitatively determining unit 12 that calculates, for example, a content of a component in the sample 3 on the basis of the energy spectrum obtained by the multichannel pulse height analyzer 11. Specifically, at least a part of the X-ray detection signal processing device 10, the multichannel pulse height analyzer 11, and the quantitatively determining unit 12 is implemented as a computer and an input/output device connected thereto.

The detection unit 9 includes: a spectroscopic device 5 that monochromates secondary X-rays 4 generated from the sample 3; and an X-ray detector 7 that generates, for each of secondary X-rays 6 obtained by the monochormating, a signal (pulse) having a pulse height corresponding to energy (wavelength) thereof such that the number of generated signals corresponds to the intensity of the secondary X-rays 6 obtained by the monochromating. As the detection unit 9 using the spectroscopic device 5, there are a fixed-type detection unit in which the wavelength of the secondary X-rays 4 to be detected is fixed, and a scanning-type detection unit that can scan the wavelength of the secondary X-rays 4 to be detected. The type and the number of the detection unit may be determined as necessary. Further, an X-ray detector, having a high energy resolution, which does not use the spectroscopic device 5 may be used as the detection unit. In the X-ray fluorescence spectrometer, the X-ray detection signal processing device 10 described above is used, so that the same operation and effect as described above can be obtained. The X-ray fluorescence spectrometer is also an embodiment of the present invention, and is included in the present invention. Further, an X-ray analyzing apparatus (for example, X-ray diffractometer), other than the X-ray fluorescence spectrometer, which uses the X-ray detection signal processing device of the present invention, is also included in the present invention.

Although the present invention has been fully described in connection with the preferred embodiments thereof with reference to the accompanying drawings, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

7 . . . X-ray detector

10 . . . X-ray detection signal processing device

13 . . . preamplifier
13a . . . CR circuit
14 . . . high-speed AD converter
15 . . . clock oscillator
16 . . . signal processing section
17 . . . comparator
18 . . . control section

What is claimed is:

1. An X-ray detection signal processing device to which a signal from an X-ray detector is inputted, and which outputs a signal having a pulse height corresponding to energy of X-rays which are incident on the X-ray detector, the X-ray detection signal processing device comprising:
   a preamplifier configured to amplify the signal from the X-ray detector, and attenuate the signal according to a time constant of a capacitor-resistor (CR) circuit;
   a dock oscillator;
   a high-speed analog-to-digital (AD) converter configured to operate based on oscillation of the dock oscillator and subject a signal from the preamplifier to high-speed AD conversion;
   a signal processing circuit configured to determine, based on rising of a signal from the high-speed AD converter, that the signal from the high-speed AD converter has arrived, and smooth the signal from the high-speed AD converter which is determined to have arrived, by using a filter function;
   a comparator configured to output a High signal when a level of the signal from the preamplifier does not exceed a predetermined upper limit value, and output a Low signal when the level of the signal from the preamplifier exceeds the predetermined upper limit value; and
   a control circuit configured to control output of one of the High signal and the Low signal of the comparator to the dock oscillator,
   wherein when the output of the comparator shifts from the Low signal to the High signal, the control circuit is further configured to delay output of the High signal to the dock oscillator until the output of the comparator is the High signal for more than a predetermined time, and
   wherein when the output of the comparator is the Low signal, the control circuit is further configured to stop oscillation by controlling the Low signal to be output to the dock oscillator, and thus stop the high-speed AD conversion by the high-speed AD converter, such that the high-speed AD converter maintains an output value obtained immediately before the stopping of the high-speed AD conversion.

2. An X-ray analyzing apparatus comprising the X-ray detection signal processing device as claimed in claim 1.

* * * * *